United States Patent [19]
Prosl

[11] Patent Number: 5,868,717
[45] Date of Patent: *Feb. 9, 1999

[54] DUAL-LUMEN CATHETER AND METHOD OF USE

[75] Inventor: Frank R. Prosl, Duxbury, Mass.

[73] Assignee: Biolink Corporation, Middleboro, Mass.

[*] Notice: This patent issued on a continued prosecution application filed under 37 CFR 1.53(d), and is subject to the twenty year patent term provisions of 35 U.S.C. 154(a)(2).

[21] Appl. No.: 631,801

[22] Filed: Apr. 10, 1996

[51] Int. Cl.⁶ .............................. A61M 5/00; A61M 25/00
[52] U.S. Cl. ................................................ 604/264; 604/4
[58] Field of Search ........................... 604/43, 265, 178, 604/280, 4, 264, 53, 24, 273

[56] References Cited

U.S. PATENT DOCUMENTS

| | | | |
|---|---|---|---|
| 4,846,791 | 7/1989 | Hattler et al. | 604/43 |
| 5,106,368 | 4/1992 | Uldall et al. | 604/43 |
| 5,221,255 | 6/1993 | Mahurkar et al. | 604/43 |
| 5,380,276 | 1/1995 | Miller et al. | 604/28 |
| 5,451,206 | 9/1995 | Young | 604/43 |
| 5,472,418 | 12/1995 | Palestrant | 604/43 |
| 5,486,159 | 1/1996 | Mahurkar | 604/4 |

*Primary Examiner*—John G. Weiss
*Assistant Examiner*—Ki Yong O
*Attorney, Agent, or Firm*—Edwin H. Paul; Jerry Cohen

[57] ABSTRACT

A dual-lumen catheter is disclosed that allows access to the vascular system of humans or animals for the high volume fluid flow related to hemodialysis or therapeutic apheresis. One lumen is circular with a wall thickness and material such that the lumen remains open during the fluid exchange. The second lumen is relatively thin walled designed to collapse against the first lumen under the pressure associated with the vascular system. This collapsing provide a minimum cross section of the catheter as it enters the body and the vascular system. However, the second lumen opens under pressure as a high volume fluid flow is introduced into the vascular system through the second lumen. This high volume fluid flow into the body is most often a return of fluid removed from the body via the thicker walled lumen.

4 Claims, 1 Drawing Sheet

DUAL-LUMEN CATHETER AND METHOD OF USE

FIELD OF THE INVENTION

The present invention relates generally to dual-lumen catheters that allow access to the vascular system of a human (or other animal) for the high volume blood flow related to fluid exchange therapies, such as hemodialysis or therapeutic apheresis.

BACKGROUND OF THE INVENTION

There exists a class of devices for accessing fluid spaces and vessels within a human (or animal) body that are generally referred to as "catheters". Herein, "vessel" is defined as any conduit carrying a fluid within the patient's body. These prior art devices comprise flexible tubes of fluid-impermeable material, and are often provided with functional apparati suited to various purposes, such as attachment, flowpath regulation (i.e., valving), etc.

Catheters are an essential component of any fluid exchange therapeutic device. Although it is known to percutaneously implant one or two catheters into a patient, thereby allowing repeated access to the patient's circulatory system, the high incidence of infection, stenosis, patient discomfort, and site/device failure has led to a search for a dual-lumen catheter that provides effective and reliable longterm operation.

A primary method of performing fluid exchange therapy, such as hemodialysis or therapeutic apheresis uses a dual-lumen catheter. The catheter is placed partially with the body with the distal end placed in a blood vessel and the proximal end outside the body. The proximal end is connected to a blood processing machine. One lumen of the catheter is for removing blood from the vessel and bringing it to the machine, and the other lumen returns blood that has been processed back to the body.

Low fluid resistance and low flow velocity in the laminar flow regime (rather than turbulent flow) are desirable because these glow attributes lessen damage to cellular components in the blood. To reduce fluid resistance, flow velocity, and maintain laminar region with high flow rate, which is now the trend, requires the lumen diameter to increase. However, practical limits exist because of the limited space within the blood vessels containing the catheters. As one increases the outside dimensions of the catheter, a reduced flow area is left for flow of blood within the vessel. This leads to blood flow disturbances within the vasculature and can lead to stenosis and thrombosis within the blood vessels. Reduced flow area can also result in an inability to withdraw the prescribed amount of blood required for effective hemodialysis therapy. Patient tolerance and discomfort are also significant considerations.

U.S. Pat. No. 5,106,368, entitled "COLLAPSIBLE LUMEN CATHETER FOR EXTRACORPOREAL TREATMENT" and issued 21 Apr. 1992 to Uldall et al. (the '368 patent), shows a dual-lumen catheter with a double-barrel shotgun configuration when disposed in vivo. A first lumen is defined by a relatively thicker wall, while a second lumen is defined by a relatively thinner wall that is collapsible against the thicker first wall for ease of insertion into a blood vessel. This insertion is accomplished by collapsing the relatively thinner wall of the catheter against the relatively thicker wall so that the entire catheter may be disposed within a peel-away sheath having a cross-sectional area smaller than that of the expanded catheter.

Uldall et al. disclose that this thinner wall is able to withstand the positive pressure required for fluid return and, further, the negative pressure required for fluid withdrawal, allowing the flows to be reversed without collapsing the lumen. Thus, once the '368 catheter is inserted, it retains its fully expanded shape and does not experience lumen collapse, during either dialysis or latency.

The overall cross-sectional shape of the Uldall et al. catheter is either "figure-8" shaped or ellipsoid. However, because these lumens must each have a sufficient cross-sectional area to accommodate fluid flowrates of up to 500 cc/min, the catheter unavoidably must have a significant external cross-sectional diameter, leading to the same adverse effects described above.

Another dual-lumen catheter is disclosed in U.S. Pat. No. 5,380,276, entitled "DUAL LUMEN CATHETER AND METHOD OF USE" and issued 10 Jan. 1995 to Miller et al. (the '276 patent). The '276 patent describes a dual-lumen catheter tube having two coaxial lumens defined by a substantially circular outer wall member separated by a substantially circular inner common support wall that joins the outer wall member. One lumen is substantially circular in cross-section, while the other is crescent-shaped in cross-section and substantially surrounds the first lumen. While the coaxial configuration of the Miller et al. '276 device addresses the known problems associated with a large diameter cross-sectional shape, the construction chosen presents other problems not seen in other devices.

First, the walls of the '276 device are of equal thickness. Miller et al. disclose that the crescent-shaped lumen may be used for removing blood from a dialysis patient and that the circular lumen may be used for blood return to the patient. This arrangement will not work in practice. The negative pressures created by dialysis machines necessary to remove blood at the rate of 500 cc/min would immediately cause the outer wall defining the crescent-shaped lumen to collapse against the inner support wall.

Miller et al. do disclose that the device may be used in a reverse manner, with fluid withdrawal accomplished via the circular lumen and fluid return via the crescent-shaped lumen. However, in a device meeting the dimensions required by the '276 disclosure, even this arrangement would result in the immediate collapse of the circular lumen, due to the same large negative pressures created during dialysis. Further, if the walls of the device were thickened so that such pressures would not collapse the respective lumens, the overall diameter of the catheter would be outside the recited ranges and the benefits of the coaxial structure vis-à-vis other known structures would be forfeited. Alternately, if the walls were constructed of a material sturdy enough to withstand these pressures, the catheter would be unacceptably stiff, resulting in a range of complications, including access site trauma, infection, and patient discomfort.

The main problem common to known twin catheters or double-lumen catheters introduced into the internal jugular vein (which is now the preferred entry point for hemodialysis) is that they occupy a large cross-sectional area in the vein. Thus the maximum outer diameter of the catheter is limited, so as to avoid an increase that is unacceptable in blood shear rate in the vessel containing the catheter. As a result of the limitation on the outer catheter diameter, the catheter lumen diameter is also limited. However, limiting the catheter lumen diameter often results in stenosis, thrombosis, platelet activation, and other problems associated with bloodflow through the catheter. Such limitations also limit the fluid flows possible, thereby limiting efficiency and reducing the possibility of decreasing treatment time.

Accordingly, it is an object of this invention to overcome the above illustrated inadequacies and problems of extant dual lumen catheters by providing an improved dual lumen catheter suitable for repeated use in applications (e.g., hemodialysis) requiring blood flowrates of 250–500 ml/min or greater.

It is another object of this invention to provide a dual-lumen catheter wherein one lumen is collapsed due to physiological pressure when the catheter is not in use.

A still further object of the present invention is to provide a dual lumen catheter that does not present an increase in blood shear rate, thereby avoiding stenosis, thrombosis, platelet activation, and other problems.

Yet another object of the present invention is to provide a dual-lumen catheter having lumens of sufficient cross-sectional area so as not to limit the efficiency of hemodialysis therapy and reduce patient treatment time.

SUMMARY OF THE INVENTION

The objects of the present invention are met by a partially collapsible, dual-lumen catheter that allows access to the vascular system of a human (or other animal) for the high-volume fluid flow related to fluid exchange therapies, such as hemodialysis or therapeutic apheresis. More particularly, the invention relates to a catheter having a) a first lumen that is substantially circular in cross-section and which is defined by the inner surface of a tubular first wall of sufficient thickness to withstand the negative pressures necessary to provide high fluid withdrawal rates, the tubular first wall preferably having a thickness of about 0.8 mm to about 1.5 mm; and b) a second lumen that is defined by the outer surface of the tubular first wall and the inner surface of a second wall of sufficient thickness to withstand positive pressures related to fluid return, yet also able to collapse against the tubular first wall in response to external, physiological body pressure when the catheter is in a latency phase, i.e., when it is not in use.

It is intended that the first lumen, defined by the tubular first wall, will be used to withdraw fluid from the patient. It is also intended that the second lumen, defined by the second wall, will be used to return fluid to the patient. Accordingly, these lumens will be referred to as the "arterial line" and the "venous line," respectively.

During the latency phase, i.e., when the device is not in use, the portion of the venous line disposed within the accessed vessel is collapsed by physiological pressure into a relatively small cross section. In this phase, the catheter occupies significantly less cross-sectional space within the vessel than conventional double-lumen catheters, thereby increasing patient comfort and tolerance for the implanted device. This geometry therefore allows for an increase in the outside diameter of the tubular first wall and, thus, a concomitant increase in the arterial line diameter, while still occupying less of the vessel's cross-sectional flow area than do conventional dual-lumen catheters. The increased cross-sectional diameter of the arterial line will lower the flow resistance in this line. During the treatment phase, an extracorporeal pump provides the necessary positive pressure to re-expand the venous line and create the flow passage for the return blood.

The catheter described can be used with the Dialock™ subcutaneous access device described in my copending U.S. patent application, Ser. No. 08/485,498 filed 7 Jun. 1995, or can be used similarly to the percutaneous catheters currently in widespread use. The collapsible catheter line can take several forms. Other objects, features and advantages will be apparent from the following detailed description of preferred embodiments thereof taken in conjunction with the accompanying drawings in which:

DETAILED DESCRIPTION OF EMBODIMENTS

Figure 1A:
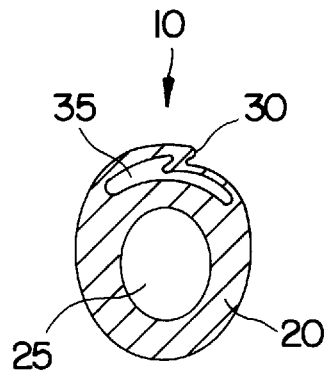
FIG. 1A shows a cross-sectional view of an embodiment of the catheter of the present invention, showing the catheter's latency phase.

As shown in FIG. 1, in a first embodiment the catheter 10 is constructed so that a first wall 20, defines a first lumen 25, of a thickness sufficient to maintain the diameter of the first lumen 25 even under low or negative internal pressure conditions. For hemodialysis operations where flowrates of 500 ml/min are common, the flow diameter of the first lumen 25 can be from 1.8 mm to 2.5 mm. A second wall 30, defines a second lumen 35, substantially thinner than the first wall 20, lying external to the first wall 20 and formed therefrom.

Figure 1B:
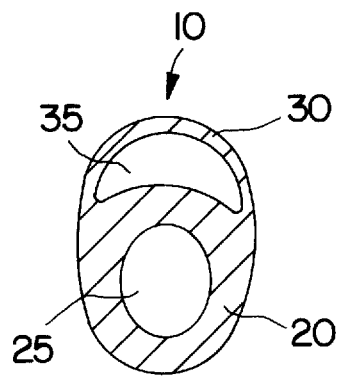
FIG. 1B shows a cross-sectional view of the catheter of FIG. 1A, showing the catheter in use.

Because the second wall 30 is substantially thinner than the first wall 20, the second wall 30 is able to fold into a smaller cross-section by external pressure when the second lumen 35 is not internally pressurized. Thus, in the quiescent state, shown in FIG. 1A, the catheter 10 occupies approximately the same cross-sectional size as conventional single-lumen catheters. When the second lumen 35 is internally pressurized, either during use or when filled with fluid, as shown in FIG. 1B, the second lumen 35 expands, albeit not to the point where the total cross-sectional size of the catheter 10 is as large as conventional double-lumen catheters.

It will now be apparent to those skilled in the art that other embodiments, improvements, details and uses can be made consistent with the letter and spirit of the foregoing disclosure and within the scope of this patent, which is limited only by the following claims, construed in accordance with the patent law, including the doctrine of equivalents.

What is claimed is:

1. A partially collapsible, dual-lumen catheter that allows access to the vascular system of a human (or other animal) for the high-volume fluid flow rates related to fluid exchange therapies, such as hemodialysis or therapeutic apheresis, the catheter comprising:

a) a tubular first wall having an inner surface and an outer surface, said tubular first wall inner surface defining a first lumen that is substantially circular in cross-section and said tubular first wall being of sufficient thickness to withstand the negative pressures necessary to provide high fluid withdrawal rates from said vascular system; and b) a second wall having an inner surface and an outer surface, said second wall inner surface and said tubular first wall outer surface defining a second lumen and said second wall being of sufficient thickness to withstand the positive pressures related to high fluid return rates, but said second wall, when said catheter is inserted into a body blood vessel, is collapsed unless said second lumen is internally pressurized.

2. The catheter, as claimed in claim 1, wherein said tubular wall has a thickness of about 0.8 mm to about 1.5 mm, and wherein said second wall has a thickness substantially less that 0.8 mm.

3. The catheter, as claimed in claim 1, wherein said first and second lumens can accommodate fluid flow rates of 200–500 cc/min.

4. A partially collapsible, dual-lumen catheter that allows access to the vascular system of a human (or other animal) for the high-volume fluid flow rates related to fluid exchange therapies, such as hemodialysis or therapeutic apheresis, the catheter comprising:

a) a tubular first wall having an inner surface and an outer surface, said tubular first wall inner surface defining a first lumen that is substantially circular in cross-section and said tubular first wall being of sufficient thickness to withstand the negative pressures necessary to provide high fluid withdrawal rates from said vascular system; and b) a second wall having an inner surface and an outer surface, said second wall inner surface and said tubular first wall outer surface defining a second lumen, and c) means for constructing said second wall of a sufficient thickness to withstand the positive pressures related to high fluid return rates, but of a thickness such that said second wall, when said catheter is inserted into a body blood vessel, is collapsed unless said second lumen is internally pressurized to overcome the physiological pressure in said body blood vessel.

* * * * *